United States Patent [19]

Verbruggen

[11] Patent Number: 5,268,163
[45] Date of Patent: Dec. 7, 1993

[54] METHOD OF PREPARING A RADIOLABELLED TECHNETIUM COMPLEX AND KIT FOR PERFORMING SAID METHOD

[75] Inventor: Alfons Verbruggen, Leuven, Belgium

[73] Assignee: Mallinckrodt Medical, Inc., St. Louis, Mo.

[21] Appl. No.: 934,648

[22] PCT Filed: Apr. 10, 1991

[86] PCT No.: PCT/US91/02450
 § 371 Date: Aug. 21, 1992
 § 102(e) Date: Aug. 21, 1992

[30] Foreign Application Priority Data

Apr. 17, 1990 [EP] European Pat. Off. ........... 90200928

[51] Int. Cl.$^5$ ............................................. A61K 49/02
[52] U.S. Cl. ..................................... 424/1.1; 534/14
[58] Field of Search ........................... 424/1.1; 534/14

[56] References Cited

U.S. PATENT DOCUMENTS

| 4,571,430 | 2/1986 | Byrne et al. | 424/1.1 |
| 4,849,511 | 7/1989 | Verbruggen | 424/1.1 |
| 4,925,650 | 5/1990 | Nosco et al. | 424/1.1 |

*Primary Examiner*—Robert L. Stoll
*Assistant Examiner*—John M. Covert
*Attorney, Agent, or Firm*—Brian K. Stierwalt

[57] ABSTRACT

The invention relates to a method of preparing a radiolabelled technetium complex by bringing Tc-99m in the form of a pertechnetate solution in a complex-forming reaction with a compound of the general formula

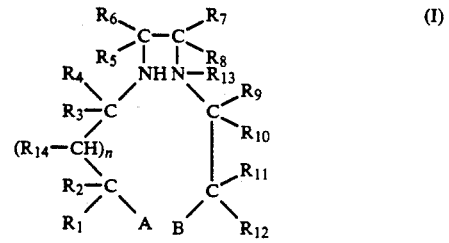

wherein $R_1-R_{12}$ each independently represents a hydrogen atom, a $C_1-C_4$ alkyl group, a carboxy group, or a carboxy($C_1-C_4$)alkyl group;
or wherein
 $R_1+R_2$, $R_3+R_4$, $R_5+R_6$, $R_7+R_8$, $R_9+R_{10}$ and $R_{11}+R_{12}$ each independently represent an oxo or imino function;
and wherein furthermore:
 $R_{13}$ is a hydrogen atom, a $C_1-C_4$ alkyl group or a carboxy($C_1-C_4$)alkyl group;
 $R_{14}$ is a hydrogen atom or an amino group; n is 0, 1 or 2;
 A represents an amino group or a mercapto group; and
 B represents a mercapto group, or a group of the general formula NH—Z—CO—NH—$_m$-Z—COOH, wherein:
  Z is an optionally substituted $C_1-C_4$ alkylene, cycloalkylene or alkylidene group, and
  m is an integer from 0 to 20;
with the provisos:
 (i) that at least one substituent selected from the group consisting of $R_1-R_{13}$ and B is or comprise a carboxy group; and
 (ii) that $R_3+R_4$ or $R_7+R_8$ represents an oxo function or both $R_3+R_4$ and $R_7+R_8$ or both $R_5+R_6$ and $R_7+R_8$ represent oxo functions, if A is an amino group and B is a group of the formula NH—Z—CO—NH—$_m$Z—COOH;
by performing said reaction in the presence of Sn(II) as a reducing agent, in the absence of a transfer agent, in an at least substantially aqueous solvent system having a pH of at least 10, and at ambient temperature.

The invention further relates to a kit for performing said method.

9 Claims, No Drawings

METHOD OF PREPARING A RADIOLABELLED TECHNETIUM COMPLEX AND KIT FOR PERFORMING SAID METHOD

The invention relates to a method of preparing a radiolabelled technetium complex by bringing Tc-99m in the form of a pertechnetate solution in a complex-forming reaction with a compound of the general formula

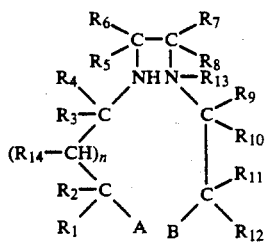
(I)

wherein $R_1$–$R_{12}$ each independently represents a hydrogen atom, a $C_1$-$C_4$ alkyl group, a carboxy group, or a carboxy($C_1$-$C_4$>alkyl group;
or wherein:
$R_1+R_2$, $R_3+R_4$, $R_5+R_6$, $R_7+R_8$, $R_9+R_{10}$ and $R_{11}+R_{12}$ each independently represent an oxo or imino function;
and wherein furthermore:
$R_{13}$ is a hydrogen atom, a $C_1$-$C_4$ alkyl group or a carboxy($C_1$-$C_4$)alkyl group;
$R_{14}$ is a hydrogen atom or an amino group;
n is 0,1 or 2;
A represents an amino group or a mercapto group; and
B represents a mercapto group or a group of the general formula NH—Z—CO—NH—$_m$—COOH, wherein:
Z is an optionally substituted $C_1$-$C_4$ alkylene, cycloalkylene or alkylidene group, and
m is an integer from 0 to 20;
with the provisos:
(i) that at least one substituent selected from the group consisting of $R_1$-$R_{13}$ and B is or comprises a carboxy group; and
(ii) that $R_3+R_4$ or $R_7+R_8$ represents an oxo function or both $R_3+R_4$ and $R_7+R_8$ or both $R_5+R_6$ and $R_7+R_8$ represent oxo functions, if A is an amino group and B is a group of the formula NH—Z—CO—NH—$_m$Z—COOH.

If Z is a substituted alkylene, cycloalkylene or alkylidene group, said group is substituted with one or more substituents selected from phenyl; phenyl substituted with.. one or more substituents selected from hydroxy, halogen and substituted phenoxy; hydroxy; mercapto; thio; methylthio; carboxy; imino; amino; amido; imidazolyl; and indolyl.

Such a complex-forming reaction as defined above, starting, however, from a compound of formula I wherein optionally mercapto groups are protected, is described in European patent application publ. no. 173424. According to this patent publication, Tc-99m mercaptoacetyltriglycine is prepared by heating a mixture of benzoyl mercaptoacetyltriglycine, an exchange ligand, a SN(II) salt as a reducing agent and a Tc-99m pertechnetate solution in a boiling water bath for five minutes. According to European patent application, publ. no. 250013, related compounds like Tc-99m mercaptoacetylglycylserylglycine are prepared in a corresponding manner, viz. by heating the S-benzoyl mercapto compound together with a SN(II) salt, Tc-99m pertechnetate and a buffer solution (pH 5.0) in a boiling water bath for 10 minutes. According to this latter European patent publication such technetium-99m complexes can also be prepared starting from the corresponding ethyl ester, viz. by heating said ester in a boiling water bath in the presence of sodium dithionite as a reducing agent in the presence of a base, apparently to saponify the ester to the correspondingg acid. As a matter of fact, however, SN(II) salts are preferred to dithionite as reducing agent in the labelling reaction with Tc-99m pertechnetate, because dithionite is not sufficiently stable under the normal storage conditions and therefore less attractive for pharmaceutical purposes.

In various respects the reaction conditions for the preparation of the radiolabelled technetium complex, as described in the above patent publications, are unsatisfactory. Usually the labelling reaction is carried out by the user himself, applying Tc-99m pertechnetate from .3 molybdenum-technetium generator that is at his disposal. It stands to reason that such operations to be carried out with radioactive material under aseptic conditions, which operations should often be performed in a clinic or clinical laboratory, should be as simple as possible to avoid any risks as to contamination of the pharmaceutical composition to be prepared and as to accidental radioactive contamination of the environment. Use of a boiling water bath for performing the above reaction is therefore a disadvantage. It would be highly favorable to be able to perform said complex-forming reaction at room temperature. Such favorable reaction conditions, however, should not be to the detriment of the reaction time. Preferably the labelling reaction should result in the desired product in a high yield only after 5 to 10 minutes at room temperature. Another disadvantage is the application of a so-called transfer agent, also defined as transfer ligand or exchange ligand, which is generally used to perform the desired complex-forming reaction. Although the labelling yield may sometimes be improved by using such a transfer agent, said agent will contaminate the final pharmaceutical composition and generally has an adverse influence on the reaction rate. Moreover, it is a disadvantage that in the complex-forming reaction described in the above European patent applications a compound is used as a starting material wherein the mercapto group is protected, e.g. by a benzoyl group. As a matter of fact, this protective group should be removed and thus may contaminate the final product.

It is the object of the present invention to provide a method of preparing a radiolabelled technetium complex, in which the above disadvantages do not occur.

This object can be achieved by a method as defined in the opening paragraph, which method is characterized according to the present invention, in that said complex-forming reaction is performed in the presence of 3n(II) as a reducing agent, in the absence of a transfer agent, in an at least substantially aqueous solvent system having a pH of at least 10, and at ambient temperature.

It has been found that under the above favorable reaction conditions of the present invention indeed in a reaction time of 5 to 10 minutes the complex-forming reaction is complete, yielding the desired radiolabelled product in a high yield and purity. Examples of suitable Sn(II.) salts which can be used as reducing agents in the above reaction are stannous chloride and stannous fluoride.

A basic environment for the radioactive labelling of certain amine ligands with technetium-99m has been investigated by Volkert et al. (J. Appl. Radiat. Isot. 33. 1982, 891–896) and by Troutner et al. (J. Nucl. Med. 21, 1980, 443–448). In the reaction described by Volkert et al., however, a ligand transfer is included, resulting in a reaction time of 30 minutes to accomplish the desired ligand exchange. The used exchange ligands are tartrate, DTPA and citrate. Troutner has used cyclam as a complexing ligand, both with and without tartrate as an exchange ligand. Reaction temperature and reaction time are not mentioned in this publication. It should be emphasized, however, that cyclam as a ligand for technetium-99m is not well comparable with the complexing compound of the general formula I defined above. Cyclam is a tetra-azacyclo-tetradecane, so a macrocyclic compound having four secondary amino functions. Therefore cyclam is to be considered as a strong base which undergoes easily deprotonation at a high pH. The compound of formula I to be used for complexing Tc-99m in the method of the invention, on the contrary, comprises, in addition to a-least one carboxy group, at least one mercapto function and/or amide function for chelating the radioactive metal ion, which functions do not show basic characteristics. Hence the complexing characteristics of cyclam differ fundamentally from those of the compound of general formula I as defined above, as also appears from the structure of the final technetium-99m complex formed.

More in particular the present invention relates to a method as defined hereinbefore, wherein for the complexforming reaction preferably is used a compound of the general formula

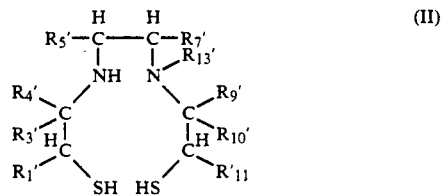

wherein $R_3'$, $R_4'$, $R_9'$ and $R_{10}'$ each independently represents a hydrogen atom, a methyl group, a carboxy group or a carboxymethyl group; or wherein $R_3'+R_4'$ and $R_9'+R_{10}$ each independently represent an oxo function;

and wherein furthermore:

$R_1'$, $R_5'$, $R_7'$ and $R_{11}'$ each independently represents a hydrogen atom, a methyl group, a carboxy group or a carboxymethyl group; and $R_{13}'$ is a hydrogen atom, a methyl group or a carboxymethyl group;

with the proviso, that at least one substituent selected from the group consisting of $R_1'$, $R_3'$, $R_4'$, $R_5'$, $R_7'$, $R_9'$, $R_{10}'$, $R_{11}'$ and $R_{13}'$ is or comprises a carboxy group.

Examples of the latter compounds are $N_2S_2$ compounds, such as carboxy group-comprising diaminedithiols or dimercaptodiamides, for example 2,3-bis(mercaptoacetylamino)propanoic acid and 1,2-ethylenedicysteine.

The method of the invention is also particularly suitable for complexing Tc-99m with a compound of the general formula

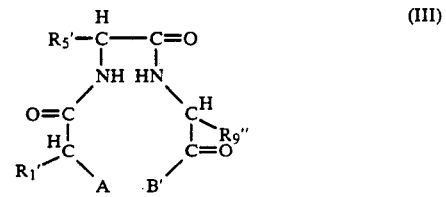

wherein $R_1'$, $R_5'$ and $R_9''$ each independently represents a hydrogen atom, a methyl group, a carboxy group or a carboxymethyl group;

A has the above meaning; and

B' represents a group of the general formula NH—Z'—COOH, wherein Z' is a $C_1$-$C_4$ alkylene or alkylidene group.

Suitable examples of the last-mentioned preferred compounds are disclosed in the European patent applications mentioned before, viz. publ. nos. 173424 and 20013, like mercapto-acetyltriglycine (MAG3), tetraglycine and mercaptoacetyl-glycylalanylglycine (MAGAG). It is indeed a real surprise that such compounds, which comprise even three amide functions for chelating Tc-99m, so readily complex this metalradionuclide ion at room temperature under the conditions defined above.

It has been found that the last-mentioned preferred method can be performed excellently at a pH of at least approximately 12.

As mentioned before, it is often more convenient to place the material to be labelled at the user's disposal, viz. in the form of a so-called kit, so that the user himself can prepare the desired radiolabelled technetium complex. For this purpose, the various non-radioactive ingredients are then offered to the user in the form of a "cold" kit. As asserted above, the operations to be carried out by the user should be as simple as possible, in order to enable him to prepare from said kit the Tc-99m labelled compound by using the facilities that are at his disposal.

Because the method of the present invention can be performed in a so simple and easy manner, viz. even without heating the reaction mixture, said preparation method can be carried out very well by the user himself. Therefore the invention also relates to a kit for performing said method, comprising (i) in an optionally dry condition a compound as defined hereinbefore, to which, if desired, an inert pharmaceutically acceptable carrier and/or a formulating agent and/or one or more auxiliary substances is/are added, (ii) a SN(II) salt (as a reducing agent), (iii) a basic substance, said ingredients (i), (ii) and/or (iii) optionally being combined, (iv) a neutralizing agent in the form of an acid or buffering substance, and (v) instructions for use with a prescription for reacting ingredients (i), (ii) and (iii) of the kit with technetium-99m in the form of a pertechnetate solution as described above, followed by a neutralization to a pH suitable for intravenous or subcutaneous administration by adding said agent defined sub (iv). Suitable neutralizing agents defined sub (iv) are mineral acids like hydrochloric acid and phosphoric acid, or buffer solutions such as phosphate buffer, acetate buffer or citrate buffer.

The ingredient of the kit mentioned sub (i) may be supplied as a solution, for example in the form of a physiological saline solution, or in some buffer solution, but may also be present in a dry condition, for example in a lyophilized condition. When used as a component for an injection liquid, this ingredient may be in a sterile condition, or, alternatively, the injection liquid may be sterilized before administration. In case the above ingredient is in a dry condition, the user may use a sterile physiological saline solution as a solvent therefor. If desired, the above-mentioned ingredient may be stabilized in the usual way with suitable stabilizers like ascorbic acid, gentisic acid or salts of these acids, or may be provided with other auxiliaries like fillers.

The invention will now be described in more detail with reference to the ensuing specific examples.

EXAMPLE I

Preparation of Tc-99m MAG3 star tine from benzoylmercartoacetyltriglycide

A. Preparation of labelling kits

To 25 mg benzoylmercaptoacetyltriglycine is added 25 ml 0.1 molar phosphate buffer pH 10.5 and the mixture is heated for 10 min in a water-bath at 100° C. After cooling 2.5 mg $SnCl_2 \cdot H_2O$ dissolved in 0.5 ml ETOH is added and the pH is adjusted to pH 12 with NAOH 1N. The solution is diluted to 25 ml with water and dispensed in 1 ml-aliquots in reaction vials. The labelling kits are lyophilized, stoppered under vacuum and then stored at 4°-8° C.

B. Preparation of Tc-99m MAG3

To a labelling kit, obtained as described under (A), is added 1 ml to 6 ml generator eluate, containing 10 mCi to 100 mCi Tc-99m in the form of pertechnetate. The contents are mixed and the vial is incubated for 5 min at room temperature.

C. Analysis of the labelling reaction mixture by reverse phase HPLC and TLC

Twenty five µl of the reaction mixture, obtained as described under Example IB, is applied at the top of a Hypersil ® 5 µm ODS column (250 mm×4.6 mm) that is eluted with gradient mixtures of 0.0125 M phosphate buffer pH 5.85 and ethanol (0 min to 15 min: 0% to 20% ethanol, 15 min to 20 min: 20% to 50% ethanol, 20 min to 30 min: 50% to 90% ethanol).

Radioactivity in the eluate is monitored by a 2 inch NaI(Tl)scintillation detector, coupled to an amplifier, single channel analyzer and Ramona ® integrating system. A typical retention time of Tc-99m MAG3 is about 13 min, depending on the configuration of the HPLC-system. This retention time is identical to that of Tc-99m MAG3 obtained by exchange labelling in the presence of tartrate. The preparation is analyzed for colloidal technetium-99m by TLC on ITLC-SG, eluted with acetonitrile-water (1:1). Typical labelling yields using the described procedure are 95–98%. Labelling is unsuccessful if the pH during labelling is inferior to pH 10.

EXAMPLE II

Preparation of Tc-99m MAG3 starting from benzylmercaptoacetyltriglycine

A. Conversion of benzylmercaptoacetyltriglycine to mercaptoacetyltriglycine 0.500 g benzylmercaptoacetyltriglycine is dissolved in 250 ml of liquid ammonia in a two-neck 500 ml-flask equipped with a cooling condenser (−75° C.) and magnetic stirrer. To the mixture is added 125 mg Na and the mixture is stirred for 15 min. The cooling condenser is then removed and the ammonia is allowed to evaporate under a stream of argon. The residue is stored under nitrogen.

B. Labelling of MAG3 with technetium-99m

To a solution of 1 mg MAG3, prepared as described under Example IIA, in 1 ml NAOH 0.1 N is added 100 µg $SnCl2-2H_2O$ dissolved in 25 µl ethanol and 2 ml generator eluate, containing 10 mCi—100 mCi Tc-99m in the form of pertechnetate. The mixture is incubated at room temperature for 10 min. Analysis of Tc-99m MAG3 is performed by the HPLC and TLC methods described under Example IC. Typical labelling yields are 88%–91% Tc-99m MAG3.

EXAMPLE III

Labelling of 2,3-bis(mercaptoacetylamino)propanoic acid with Tc-99m

A. Conversion of 2,3-bis-(benzylmercaptoacetylamino)propanoic acid to 2,3-bis(mercaptoacetylamino)propanoate ($CO_2$-DADS)

The same procedure is used as described under Example IIA, but twice the amount of sodium is used.

B. Labelling

To a solution of 1 mg $CO_2$-DADS in 1 ml NAOH 0.1 N is added 100 µg $SnCl_2$ dissolved in 25 µl ethanol and 2 ml generator eluate, containing 10 mCi—100 mCi Tc-99m in the form of pertechnetate. The mixture is incubated at room temperature for 10 min and then neutralized by the addition of 0.5 M phosphate buffer pH 5. Analysis is performed by the HPLC and TLC methods described under Example IC. Typical labelling yields are 85–90% Tc-99m $CO_2$-DADS.

EXAMPLE IV

Labelling of 1,2-ethylenedicysteine with technetium-99M

A. Labelling

To a solution of 1 mg 1,2-ethylenedicysteine in 1 ml 0.05 molar phosphate buffer pH 12 is added a solution of 100 µg $SnCl_2.2H_2O$ in 25 µl HCl 0.05 M and 1 ml to 4 ml generator eluate (10 mCi to 100 mCi Tc-99m in the form of pertechnetate). The mixture is incubated for 5 min at room temperature.

B. Analysis

25 µl of the reaction mixture is applied at the top of a Hypersil 5 µm ODS column (250 mm×4.6 mm), that is eluted with gradient mixtures of 0.025 M phosphate buffer pH 2.5 and ethanol (0 min to 6 min:0% to 9% ethanol; 6 min to 25 min:9% ethanol; 25 min to 30 min:9% to 0% ethanol). The radioactivity in the eluate is monitored by a 2 inch NaI(Tl) scintillation detector coupled to an amplifier, single channel analyzer and Ramona ® integrator. A typical retention time of Tc-99m-ethylenedicysteine is 12 min. The reaction mixture is also analyzed for the presence of colloidal technetium-99m by TLC on ITLC-SG, eluted with acetonitrile-water (1:1). Typical labelling yields in the described conditions are 98–99%. The labelling yield decreases significantly as the pH during labelling is inferior to pH 11, viz. to approx. 69 % at pH 9 and to approx. 47% at pH 7.

EXAMPLE V

A. Labelling of a tetrapeptide, viz. tetraglycine, with technetium-99m

To a solution of 1 mg tetraglycine in 1 ml 0.1 N NaOH is added a solution of 100 μg Sn Cl$_2$.2H$_2$O in 25 μl HCl 0.05 N and 1 ml to 4 ml generator eluate containing 10 mCi to 100 mCi Tc-99m in the form of pertechnetate. The mixture is incubated for 5 min at room temperature.

B. Analysis of the reaction mixture by RP-HPLC and TLC

25 μl of the reaction mixture is applied at the top of a Hypersil 5 μm ODS column (250 mm×4.6 mm) that is eluted with gradient mixtures of 0.05 M phosphate buffer pH 5.85 and ethanol as described under Example IC. A typical retention time of the Tc-99m tetraglycine complex in the described conditions is 12 min, but it can vary depending on the HPLC-configuration and column characteristics. The reaction product is also analyzed for the presence of colloidal technetium-99m (TcO$_2$) by TLC on ITLC-SG, eluted with saline or acetonitrile-water (1:1). Typical yields are 94-98%.

By the same procedure other tetrapeptides are labelled with Tc-99m, e.g. alanyltriglycine, glycylalanyldiglycine and tetra-alanine. Labelling yields are in each case over 90%.

I claim:

1. A method of preparing a radiolabelled technetium complex by bringing Tc-99m in the form of a pertechnetate solution in a complex-forming reaction with a compound of the general formula

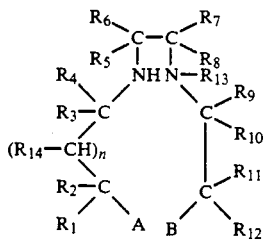

(I)

wherein R$_1$-R$_{12}$ each independently represents a hydrogen atom, a C$_1$-C$_4$ alkyl group, a carboxy group, or a carboxy(C$_1$-C$_4$)alkyl group;

or wherein

R$_1$+R$_2$, R$_3$+R$_4$, R$_5$+R$_6$, R$_7$+R$_8$, R$_9$+R$_{10}$ and R$_{11}$+R$_2$ each independently represent an oxo or imino function;

and wherein furthermore:

R$_{13}$ is a hydrogen atom, a C$_1$-C$_4$ alkyl group or a carboxy(C$_1$-C$_4$)alkyl group;

R$_{14}$ is a hydrogen atom or an amino group; n is 0, 1 or 2;

A represents an amino group or a mercapto group; and

B represents a mercapto group, or a group of the general formula NH—Z—CO—NH—$_m$-Z—COOH, wherein:

Z is an optionally substituted C$_1$-C$_4$ alkylene, cycloalkylene or alkylidene group, and m is an integer from 0 to 20;

with the provisos:

(i) that at least one substituent selected from the group consisting of R$_1$-R$_{13}$ and B is or comprises a carboxy group; and (ii) that R$_3$+R$_4$ or R$_7$+R$_8$ represents an oxo function or both R$_3$+R$_4$ and R$_7$+R$_8$ or both R$_5$+R$_6$ and R$_7$+R$_8$ represent oxo functions, if A is an amino group and B is a group of the formula NH—Z—CO—NH—$_m$Z—COOH;

characterized in that said complex-forming reaction is performed in the presence of SN(II) as a reducing agent, in the absence of a transfer agent, in an at least substantially aqueous solvent system having a pH of at least 10, and at ambient temperature.

2. A method as claimed in claim 1, by bringing Tc-99m in the form of a pertechnetate solution in a complexforming reaction with a compound of the general formula

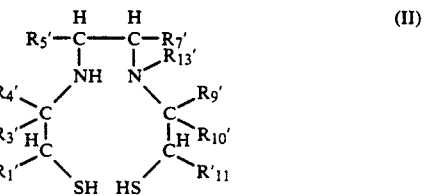

(II)

wherein R$_3'$, R$_4'$, R$_9'$ and R$_{10}'$ each independently represents a hydrogen atom, a methyl group, a carboxy group or a carboxymethyl group; or wherein R$_3'$+R$_4'$ and R$_9'$+R$_{10}$ each independently represent an oxo function;

and wherein furthermore:

R$_1'$, R$_5'$, R$_7'$ and R$_{11}'$ each independently represents a hydrogen atom, a methyl group, a carboxy group or a carboxymethyl group; and R$_{13}'$ is a hydrogen atom, a methyl group or a carboxymethyl group;

with the proviso, that at least one substituent selected from the group consisting of R,', R$_3'$, R$_4'$, R$_5'$, R$_7'$, R$_9'$, R$_{10}'$, R$_{11}'$ and R$_{13}'$ is or comprises a carboxy group; characterized in that said complex-forming reaction is performed in the presence of SN(II) as a reducing, agent, in the absence of a transfer agent, and in an at least substantially aqueous solvent system having a pH of at least 10.

3. A method as claimed in claim 1, by bringing Tc-99m in the form of a pertechnetate solution in a complex-forming reaction with a compound of the general formula

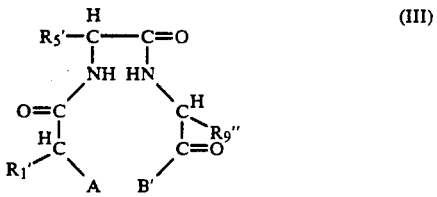

(III)

wherein R$_1'$, R$_5'$ and R$_9''$ each independently represents a hydrogen atom, a methyl group, a carboxy group or a carboxymethyl group;

A has the meaning given in claim 1; and

B' represents a group of the general formula NH—Z'—COOH, wherein Z' is a C$_1$-C$_4$ alkylene or alkylidene group;

characterized in that said complex-forming reaction is performed in the presence of Sn(II) as a reducing agent, in the absence of a transfer agent, and in an at least substantially aqueous solvent system having a pH of at least 10.

4. A method as claimed in claim 3, characterized in that the complex-forming reaction is performed at a pH of at least approximately 12.

5. A kit for performing a method as claimed in claim 1, comprising (i) in an optionally dry condition a compound of the general formula I, as presented in claim 1, wherein the symbols have the meanings given in claim 1, to which compound, if desired is added along or in combination an inert pharmaceutically acceptable carrier, a formulating agent, or one or more auxiliary substances, (ii) a Sn(II) salt (as a reducing agent), (iii) a basic substance (iv) a neutralizing agent in the form of an acid or buffering substance, and (v) instructions for use with a prescription for reacting ingredients (i), (ii) and (iii) of the kit witch technetium-99m in the form of a pertechnetate solution as described in claim 1, followed by a neutralization to a pH suitable for intravenous or subcutaneous administration by adding said agent defined in (iv).

6. A kit as claimed in claim 5, comprising as said ingredient (i) in an optionally dry condition a compound of the general formula II or III, as presented in claim 2 or 3, respectively, wherein the symbols have the meanings given in these claims, to which compound, if desired, is added along or in combination an inert pharmaceutically acceptable carrier, a formulating agent, or one or more auxiliary substances.

7. A kit as claimed in claim 5 wherein at least one of the ingredients (i), (ii) or (iii) is combined with at least one of the other ingredients (i), (ii) or (iii).

8. The kit as claimed in claim 5 wherein the Sn(II) salt is stannous chloride.

9. The kit as claimed in claim 5 wherein the Sn(II) salt is stannous fluoride.

* * * * *